United States Patent
Alving et al.

(10) Patent No.: US 6,511,425 B1
(45) Date of Patent: *Jan. 28, 2003

(54) METHOD FOR THE DIAGNOSIS OF FOOD INTOLERANCE

(75) Inventors: Kjell Alving, Uppsala (SE); Jon Lundberg, Stockholm (SE); Lennart Nordvall, Uppsala (SE); Edward Weitzberg, Stockholm (SE)

(73) Assignee: Aerocrine AB, Solna (SE)

( * ) Notice: Subject to any disclaimer, the term of this patent is extended or adjusted under 35 U.S.C. 154(b) by 141 days.

This patent is subject to a terminal disclaimer.

(21) Appl. No.: 09/712,262

(22) Filed: Nov. 15, 2000

Related U.S. Application Data

(60) Continuation-in-part of application No. 09/273,514, filed on Mar. 22, 1999, now Pat. No. 6,183,416, which is a division of application No. 08/849,282, filed on May 30, 1997, now Pat. No. 6,063,027.

(30) Foreign Application Priority Data

Nov. 16, 1999 (SE) ................................. 9904138

(51) Int. Cl.⁷ ................................. A61B 5/00
(52) U.S. Cl. ....................... 600/300; 128/898
(58) Field of Search ................. 600/300, 301; 128/897, 898, 923

(56) References Cited

U.S. PATENT DOCUMENTS 5,983,899 A  11/1999  Hällgren
6,183,416 B1 *  2/2001  Alving et al. ............... 128/898
6,387,890 B1 *  5/2002  Christianson et al. ......... 514/64

FOREIGN PATENT DOCUMENTS

WO  95/32668  12/1995
WO  96/17244  6/1996
WO  98/41153  9/1998

OTHER PUBLICATIONS

Loft et al, Rectal Gluten Challenge and diagnosis of Coeliac Disease, Lancet, vol. 335, Jun. 1990, pp. 1293–1295.*

Smith et al, Nitric Oxide Synthase Activity in Ulcerative Colitis and Crohn's Disease, Lancet, vol. 342, Aug. 1993, pp. 338–340.*

Holmgren Peterson K, et al., "Children with Celiac Disease Express Inducible Nitric Oxide Synthase in the Small Intestine during Gluten Challenge", J Gastroenterol, vol. 33, 1998, pp. 939–943.

Forte P, et al., "Nitric Oxide Synthesis in Patients with Infective Gastroenteritis", Gut, vol. 45, 1999, pp. 355–361.

Tomita R, et al., "Role of Nitric Oxide in the Colon of Patients with Ulcerative Colitis", World J. Surg., vol. 22, 1998, pp. 88–92.

Raab et al., "A Technique for Seqmental Rectaland Colonic Perfusion in Humans", The American Journal of Gastroenterology, vol.; 87, No. 10, 1992, pp. 1453–1459.

* cited by examiner

Primary Examiner—Eric F. Winakur
Assistant Examiner—David J. McCrosky
(74) Attorney, Agent, or Firm—Banner & Witcoff, Ltd.

(57) ABSTRACT

A method for the detection and diagnosis of food intolerance, e.g. coeliac disease, based on the determination of nitric oxide in a gas sample taken from the lumen of the distal gastrointestinal tract, preferably the rectum, after subjecting the patient to the suspected substance, underlying the intolerance reaction.

11 Claims, 1 Drawing Sheet

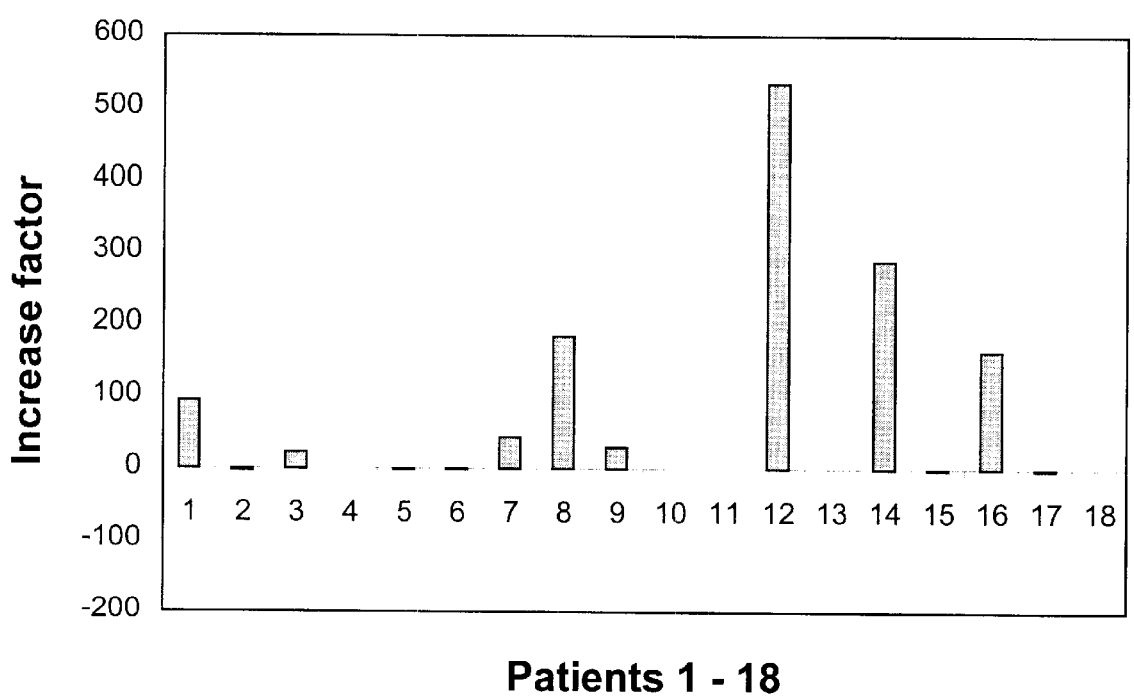
Fig. 1. Rectal NO response after rectal gluten provocation

METHOD FOR THE DIAGNOSIS OF FOOD INTOLERANCE

This application is a Continuation-in-Part of U.S. patent application Ser. No. 09/273,514, filed Mar. 22, 1999, now U.S. Pat. No. 6,183,416, which is a Divisional Application of U.S. patent application Ser. No. 08/849,282, filed May 30, 1997, now U.S. Pat. No. 6,063,027, and is based on International Application PCT/SE95/01429. This application is based upon and claims the benefit of priority from Swedish Patent Application No. 9904138-6, filed Nov. 16, 1999.

The present invention relates to a new method for the diagnosis and evaluation of adverse reactions to food, so called food intolerance, in particular coeliac disease.

BACKGROUND OF THE INVENTION

Food intolerance is an adverse reaction to a food or food component that does not involve the IgE-mediated immune response seen in classic food allergies, e.g. cow milk allergy. Food intolerance reactions can be triggered by a physical reaction to a food or food additive. For example, people with lactose intolerance do not have enough of the enzyme lactase, to digest the lactose naturally present in milk. This is one of the most common food intolerances and can be managed through diet and the use of enzyme preparations, such as Lactaid® caplets or drops. Another ailment is coeliac disease, where the patient reacts to the gluten in cereal foods.

Further, certain food additives such as flavour enhancers (mono sodium glutamate) or preservatives (sulphates) used on foods may cause a food intolerance reaction in some people. The symptoms of food intolerance vary and can be mistaken for those of a food allergy or other ailments.

Coeliac disease or malabsorption syndrome is a syndrome mainly affecting children, but also adults, caused by a reaction to gluten which prevents the small intestine from digesting fat. In adult coeliac disease, the adverse reaction to gluten is known to cause atrophy of the intestinal villi, so that the surface available for absorption becomes smaller. The symptoms of coeliac disease include a swollen abdomen, diarrhoea, abdominal pains and anemia.

It is known that intolerance to wheat gluten is a major factor in the aetiology of the enteropathy observed in almost all children with coeliac disease and most adults with idiopathic steatorrhoea. Diagnosis has frequently been based on dietary changes, namely putting the patients on a gluten-free diet and observing the possible recovery/normalisation.

The gold standard for the diagnosis of coeliac disease remains a jejunal biopsy showing typical mucosal lesions of the small intestine including villous atrophy. Biopsies may be taken before and after exclusion of gluten in the patient's diet. Following the introduction of a gluten-free diet, the intestinal mucosa will regenerate and the symptoms normally disappear.

Controlled reintroduction of gluten or a rectal gluten challenge combined with colonoscopy or the examination of a biopsy sample has been experimentally used to confirm the diagnose.

It has been suggested that coeliac disease can be diagnosed using jejunal biopsy, taken with a Watson/Crosby capsule before and after an oral FF3 challenge. FF3 (Frazer's fraction III) is a peptic-tryptic digest of gluten that is known to damage the mucosa of the small intestine in gluten-sensitive subjects. The biopsy samples are prepared and the number of intraepithelial lymphocytes is estimated. A result can be available within 24–48 h which prompts the authors to call this a "rapid confirmatory test of gluten sensitivity in patients already taking a gluten-free diet" (Loft, D. E. et al., Lancet, 335 (1990) 1293–1295).

It is known that nitric oxide (NO) is produced at many sites in the gastrointestinal tract and believed to participate in both physiological and pathological events (Whittle G. J. R., Physiology of the Gastrointestinal Tract, New York: Raven Press (1994) 267–94).

It is further known through WO 96/17244 (by Kjell Alving, Edward Weitzberg, Jan Lundberg and Jon Lundberg) that inflammatory states in the intestines can be detected by measuring the concentration of nitric oxide in a gas sample, taken from the intestinal lumen. This method has hitherto been implemented in the diagnosis of Crohn's disease and ulcerative colitis.

Further, a method and device for the diagnosis of allergies has been disclosed in U.S. Pat. No. 5,983,899, which method comprises analysing a sample that has been taken rectally from the large intestine of a patient who is suspected of being allergic, after having provoked the mucous membrane of the patient's large intestine rectally with an allergen against which the suspected allergy of the patient is directed. The method is illustrated by examples, where nine patients suffering from coeliac disease were examined using a rectal perfusion technique using a six-channel PVC hose having an inner diameter of 10 mm, an outer diameter of 16 mm and a total length of 38 cm. Three inflatable balloons were fastened to the hose, to obtain a rectal perfusion segment of 8 cm in length. Two rectal perfusions were performed on each individual on one and the same day: a basal perfusion and a perfusion three hours after introducing gluten. The participants were studied after having fasted for 17 hours and 4 liters of an oral laxative solution was used as an enema. The disclosure of U.S. Pat. No. 5,983,899 also comprises an instrument for rectal insertion in the rectum, having an expandable part which surrounds a central channel which opens out on each side of the expandable part, and a separate channel through which expansion of the expandable part can be controlled such that when the instrument is applied in the rectum; the outer wall of the expandable part will be in direct contact with the mucous membrane of the rectum; and wherein a diffusible allergen and a receptor for an inflammation marker are present on an outer defining surface of the expandable part.

In summary, it remains a problem to make available a simple, rapid, safe and reliable test for determining the occurrence of food allergy and food intolerance, and in particular a rapid method of screening patients exhibiting diffuse symptoms possible related to food allergy. Thus, there remains a need for a truly rapid, preferably non-invasive method of diagnosing food intolerance and in particular coeliac disease, not involving the need for taking biopsy samples, a preparatory cleaning of the intestines by an enema or other invasive and inconvenient steps, often very exhausting and sometimes even painful for the patient.

SUMMARY OF THE INVENTION

The present invention makes available a rapid and simple method for the diagnosis and/or evaluation of food intolerance, the evaluation of type and/or the degree of severity of a food intolerance condition, in particular coeliac disease, according to the attached claims. According to the invention, rectal NO is measured after provoking the patient rectally with the suspected food intolerance causing agent, and an increased concentration compared to values typical for healthy individuals, or for the same patient at an earlier occasion when said agent was avoided, and an increased value is taken as an indication of food intolerance. Further embodiments and advantages of the present invention will be evident from the description and examples, and the attached figure (FIG. 1) which shows the increase factor of a rectal NO response after rectal gluten provocation in 18 patients with diagnosed coeliac disease.

BRIEF DESCRIPTION OF THE DRAWINGS

FIG. 1 shows rectal nitric oxide response after rectal gluten provocation.

DETAILED DESCRIPTION OF THE INVENTION

The present invention concerns a method for the detection and diagnosis of food intolerance, e.g. coeliac disease, based on the determination of nitric oxide in the rectum or in a gas sample taken from the rectum after subjecting the patient to the suspected substance, underlying the intolerance reaction.

The present inventors have been successful in measuring NO concentrations in luminal gas sampled from the distal part of the gastrointestinal tract, in particular from the colon and/or rectum of patients with diagnosed food intolerance after a rectal provocation using the substance associated with the disease. These concentrations have been compared with base values, obtained from the same individuals before provocation. The patients with diagnosed food intolerance exhibited significantly increased NO levels whereas the healthy controls exhibited unchanged values. The inventive method was confirmed using patients with diagnosed coeliac disease, but it is conceived that the same method is applicable to other food intolerance reactions.

The expression "healthy individuals" means individuals who do not experience gastrointestinal problems associated with the substance to be tested.

The substance to be tested can be any substance suspected of causing food intolerance reactions, such as food component or ingredient, for example gluten (coeliac disease), lactose (lactose intolerance) or any other component, suspected to be the causative agent in gastrointestinal problems. For example, bio-active food compounds including saponins and glycoalkaloids from onions and potatoes respectively, have been isolated and are presently the subject for studies.

A preparation, suitable for the challenge according to the present invention, can be a solid, semisolid or liquid preparation, containing the suspected causative agent, preferably in pure form together with physiologically neutral or inactive carrier substances. As a liquid preparation, the present invention intends to also comprise sprayable preparations or foams, possible to administer in the rectum. Conventional, physiologically acceptable propellants, such as carbon dioxide, can be used. Further, physiologically acceptable carriers such as saline, glycerine, cellulose etc. can be used. Suitable adjuvants can be chosen among physiologically tolerated adjuvants, such as preservatives, colorants, disintegration agents, lubricants, encapsulating agents, waxes, cellulose, gums, antifoaming agents etc. Preferably the suspected substance is formulated as an aqueous liquid, gel or paste for rectal instillation. Alternatively, the substance is formulated as a suppository, comprising normally used pharmaceutically accepted adjuvants. Further, the sensitivity of the determination can be increased by adding L-arginine to the preparation or by administering the substrate L-arginine perorally, intravenously, or locally e.g. via a colonoscope or a catheter to enable the detection of low grade reactions.

According to a preferred embodiment, the suspected intolerance causing substance is comprised in a suppository, further comprising L-arginine and suitable carriers and adjuvants, e.g. microcrystalline cellulose.

According to another preferred embodiment, the suspected intolerance causing substance is comprised in a foam or foam forming composition, further comprising L-arginine.

According to another preferred embodiment, the suspected intolerance causing substance is bound to a matrix, minimising or preventing its uptake by the mucous membrane of the patient.

The inventive method is characterized by the following steps:
 rectally provoking or challenging a patient with a suspected food intolerance causing substance;
 measuring the NO concentration in the rectum or in a gas sample taken from the rectum;
 comparing the found concentration with a concentration obtained for healthy individuals or with the level obtained for the same individual at another occasion, where an increased level is taken as an indication of food intolerance, caused by the substance used in the provocation.

According to an embodiment of the invention, the method comprises the following steps:
 obtaining a first gas sample from the lumen of the intestines and preferably the rectum of an individual;
 determining the content of nitric oxide (NO) in said, first sample;
 subjecting the individual to a challenge or provocation, using the suspected intolerance causing substance or agent;
 obtaining a second gas sample from the lumen of the intestines and preferably the rectum of the individual;
 determining the content of nitric oxide (NO) in said, second sample; and
 comparing the found level in said second with said first level, or with the level obtained for healthy individuals or with the level obtained for the same individual at another occasion, where an increased level is taken as an indication of food intolerance, caused by the substance used in the provocation.

The challenge or provocation can be performed by either the oral route or by the rectal route. Preferably, the method comprises a step of challenging the patient rectally under controlled and repeatable conditions, with a substance, suspected of causing an food intolerance reaction.

The steps concerning the second sample, obtained after the provocation, can be repeated at pre-determined intervals after the provocation. A second and further sample or samples can be obtained e.g. at 1, 2, 4, 8, 12, 24 and 48 hours after the provocation. The information obtained by mapping the NO levels obtained at different time-points after the provocation is used for diagnostic purposes, for example to determine the type and/or severity of the intolerance reaction.

Preferably a measurement is made or a sample taken within 1 to 24 hours after the provocation, preferably about 6 to 12 hours after the rectal provocation.

An increased NO level relative the level of healthy individuals—or the same individual before provocation—is taken as an indication of an intolerance reaction in the intestines of the individual from which the sample was obtained. In case the level is compared with a level at another occasion, e.g. an earlier occasion, and found to be increased, this is an indication of a worsening of the condition. Correspondingly, a decreased level can be interpreted as improvement. The sampling and measurement techniques should of course be essentially the same for values to be compared.

In many examination and sampling methods according to the prior art, the intestinal examination is performed or the sample obtained after the entire intestinal lumen or the location concerned has been emptied and cleaned, but such a procedure is not necessary with the inventive method. The method gives reliable results in spite of the fact that the intestines can never be totally cleared from bacteria.

The sample can be taken through a catheter placed in the rectum or colon and equipped with syringes for collecting the gas, for instances during colonoscopy (colonoscopes are normally equipped with canals allowing withdrawal of gas samples from the intestinal lumen). Samples may also be taken with the same type of instrument as described by Raab et al. (Am. 3. Gastroenterol. 87 (1992) 1453–1459). See also Krog et al., (WO 91/08013). With respect to the rectum, gas samples may be directly collected for instance by aspirating rectal gas into a syringe. Samples may also be taken from the lumen of the small intestines, by using e.g. the equipment described by Odlind et al. (SE 455,368 which corresponds to WO 88/03389). The methodologies presented by both Raab et al. and Krog et al. provide the possibility of obtaining samples representative for segments of colon and rectum.

The NO content may be determined/calculated as a concentration value, absolute amount or relative some internal or external standard. The content may be expressed as values normalised against components that natively are present in intestinal gas together with NO, preferably in fairly constant levels (internal standards). The NO content may also be calculated as amount secreted per time unit when taking air flow into account. When using balloon techniques as described by Krog et al., (WO 91/08013) and Odlind et al. (SE 455,368 which corresponds to WO 88/03389) the amount found may be taken in relation to exposed mucosal area.

For out-patient sampling of intestinal air, rectal samples are preferred (although this does not exclude other type of sampling for this type of patients). Rectal sampling results in NO values which measure both rectal and colonic reactions in case gas is allowed to freely spread in the intestinal canal. By using the techniques described by Krog et al., (WO 91/08013), NO values which measure rectal reaction to various substances, suspected of causing an intolerance reaction, may be obtained.

The sample or samples can be taken in a clinic or hospital or in the home, either by medically trained personnel or by the patient him/herself. Samples can be extracted, treated, stored and/or transported for later measurements in a different location, provided that the integrity of the sample is guaranteed or that the chemical changes taking place in the sample are known.

Preferably the measurement is made in situ in the rectum, for example using a suitable sensor. According to another embodiment, the NO concentration is determined by introducing a thin catheter with an inflatable portion of NO-permeable but liquid impermeable material, inflating said inflatable portion with NO-free air or with a gas of known composition, incubating the inflated portion in the rectum, aspirating the gas from the inflatable portion and determining the NO concentration in said gas.

Methods for the determination of NO in gas samples are well known in the field. For the determination of low NO levels, NO gas analysers based on chemiluminescent detection are preferred at the priority date. See for instance Archer, FASEB J., 7 (1993) 349–60 and Alving et al., WO 9502181. One commercially available NO analyser is the MBA apparatus Aerocrine AB, Solna, Sweden). The concentration of NO can also be measured using laser- or IR-based analysers or using electrochemical sensors.

It is a well known problem that histological analysis of e.g. inflammation in a biopsy from the intestinal mucosa may not be representative for the general state of the gastrointestinal tract. Since NO in gas will be more evenly distributed, this method will correlate better with the intolerance reaction, i.e. the area of affected mucosa together with the degree of the intolerance reaction in affected areas.

By measuring the reaction related to a specific provocation, the inventive method makes available a more specific and more reliable method for the diagnosis of food intolerance reactions, as it reduces the influence of other factors such as the general state of the patient, the current diet and possibly other intolerance or allergy causing substances.

The invention will now be illustrated in closer detail in the attached example, which shows one embodiment of the invention.

EXAMPLE

The concentration of nitric oxide was determined in a gas sample taken from the rectum of patients subjected to local provocation with gluten. A group of patients with diagnosed coeliac disease (n=18, age 24–75 years) and a group of healthy controls (n=5, age 24–44 years) were subjected to a provocation and NO-measurement according to the inventive method.

A soluble gluten extract (2 g Frazer's fraction dissolved in 10 ml saline) was introduced 15 cm into the rectum via a catheter. The gluten extract was kept in place 1 hour before starting the measurements. The concentration of NO in the rectal gas was measured by introducing NO-free air in the inflatable cuff of the catheter and waiting 10 minutes, allowing NO to penetrate into the cuff. The air was withdrawn from the cuff and the concentration of NO measured using a conventional NO analyser (MBA, Aerocrine AB, Solna, Sweden). The NO-concentration was determined at 0, 2, 4, 8 and 24 hours.

The results of this study are presented in Table 1 and FIG. 1. Notably none of the controls (N=5) exhibited increased NO concentrations. Among the 18 patients with diagnosed coeliac disease, 11 exhibited more than a two-fold increase after 24 hours. The average increase, exhibited by the patients was 126 times the starting value. Surprisingly as many as 9 patients (50%) exhibited an increase above 10 times the starting value.

TABLE 1

Gluten provocation study

| Subject | Base line NO | 24 h | Change factor |
| --- | --- | --- | --- |
| Patient 1 | 51 | 4783 | 94 |
| Patient 2 | 310 | 137 | neg |
| Patient 3 | 601 | 14000 | 23 |
| Patient 4 | 82 | 152 | 1.8 |
| Patient 5 | 870 | 803 | neg |
| Patient 6 | 22 | 17 | neg |
| Patient 7 | 36 | 1600 | 44 |

TABLE 1-continued

Gluten provocation study

| Patient 8 | 76 | 14000 | 184 |
|---|---|---|---|
| Patient 9 | 27 | 750 | 30 |
| Patient 10 | 95 | 273 | 2.9 |
| Patient 11 | 119 | 1022 | 8.6 |
| Patient 12 | 43 | 23000 | 535 |
| Patient 13 | 32 | 36 | 1.1 |
| Patient 14 | 28 | 8050 | 288 |
| Patient 15 | 20 | 17 | neg |
| Patient 16 | 129 | 21000 | 163 |
| Patient 17 | 60 | 35 | neg |
| Patient 18 | 8 | 98 | 12.3 |
| Average: | 145 | 4987 | 34 |
| Responders (Factor > 2) | n = 11 | (>60%) | |
| Responders (Factor > 10) | n = 9 | (50%) | |
| Control 1 | 230 | 160 | neg |
| Control 2 | 103 | 51 | neg |
| Control 3 | 200 | 44 | neg |
| Control 4 | 130 | 118 | neg |
| Control 5 | 76 | 70 | neg |
| Responders | | 0 | 0 |

The fact that none of the controls responded with increased NO values is a strong indication that the inventive method could avoid false positive diagnosis. On the other hand, the fact that some of the patients with diagnosed coeliac disease showed a negative change at the 24 hour measurement can have several reasons. It is possible that the diagnosis is incorrect or that the disease has receded thanks to other treatment, medication or dietary changes. It is also possible that these patients exhibited a peak NO value earlier or later than the 24 hour measurement, that their NO increased was only very short and temporary and escaped detection in the present study. It is also possible that the FF3 challenge was not optimal for eliciting the right reaction in these patients. It is for example possible, that the exposure time was too short for the specific reaction pattern in these patients. Also the dose and composition of the gluten extract used in the experiments could have been less than optimal for these patients and thus be a source of error.

It is further possible that sub-groups exist among patients suffering from coeliac disease and that these subgroups exhibit different reaction patterns in a test according to the invention. In that case, the present method could make possible the differentiation between different patient groups, suffering from similar symptoms or within a group, diagnosed to suffer from coeliac disease. The present method could also function as a screening to distinguish between patients having symptoms, unrelated to gluten and patients meriting a further examination.

The measurement of NO concentration in the rectum or in a gas sample taken from the rectum has the advantage of being a reliable and also a very patient-friendly method, suitable also for small children. Measurements can also be taken by the patient himself/herself, in the patient's home.

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

What is claimed is:

1. A method for the diagnosis of food intolerance in a human patient, comprising the steps of:
   administering to the human patient a provocation using a suspected intolerance causing substance;
   measuring concentration of nitric oxide gas in the intestinal lumen of the human patient or in a gas sample taken from the rectum of the human patient; and
   comparing the concentration of nitric oxide measured to concentrations of nitric oxide obtained for healthy individuals or for the same patient at an earlier occasion;
   wherein an elevated concentration of nitric oxide as compared to concentrations of nitric oxide obtained for healthy individuals or the same patient at an earlier occasion indicates an intolerance toward the suspected intolerance causing substance.

2. The method of claim 1, wherein the patient is provoked with the suspected intolerance causing substance by administering said substance rectally to said patient.

3. The method of claim 2, wherein the suspected intolerance causing substance is administered as a gel, paste, solution, foam, spray or suppository.

4. The method of claim 2, wherein the suspected intolerance causing substance is administered as a gel, paste, solution, foam, spray or suppository which further comprises L-arginine.

5. The method of claim 1, wherein L-arginine is administered to the patient perorally, intravenously or locally, before or simultaneously with the administration of the suspected intolerance causing substance.

6. A composition for use in the method of claim 1, wherein said composition comprises a suspected food intolerance causing substance and L-arginine.

7. The method of claim 1 wherein a suspected food intolerance causing substance and L-arginine are administered.

8. A method for the diagnosis of coeliac disease, comprising the steps of:
   administrating a gluten-containing composition rectally to a patient;
   obtaining a gas sample from the rectum of the patient;
   measuring concentration of nitric oxide gas in the gas sample; and
   comparing the concentration of nitric oxide gas measured to a concentration of nitric oxide gas obtained for the patient before the administration of the gluten-containing composition;
   wherein an increase of the concentration of nitric oxide gas is an indication of coeliac disease.

9. The method of claim 8, wherein the gluten-containing composition is Frazer's fraction III (FF3).

10. The method of claim 8, wherein L-arginine is administered to the patient perorally, intravenously, or locally, before or simultaneously with the administration of the gluten-containing composition.

11. A composition comprising gluten and L-arginine.

* * * * *